US00PP36000P2

(12) United States Plant Patent
Scheffers

(10) Patent No.: US PP36,000 P2
(45) Date of Patent: Jul. 9, 2024

(54) ***YUCCA* PLANT NAMED 'YUGOSTA03'**

(50) Latin Name: *Yucca guatemalensis*
Varietal Denomination: YUGOSTA03

(71) Applicant: Dragontree Beheer B.V., Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 18/445,659

(22) Filed: Dec. 12, 2023

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
CPC ..... A01H 5/12; A01H 5/00; A01H 6/12
See application file for complete search history.

*Primary Examiner* — June Hwu
(74) *Attorney, Agent, or Firm* — Samuel R. McCoy, Jr.

(57) ABSTRACT

A new and distinct *Yucca* plant named 'YUGOSTA03' which is characterized a compact growth habit with ensiform foliage borne on a short unbranched stem, uniquely variegated foliage, and the stability of these characteristics from generation to generation.

2 Drawing Sheets

Latin name of the genus and species: The Latin name of the genus and species of the novel variety disclosed herein is *Yucca guatemalensis.*

Variety denomination: The inventive cultivar of *Yucca* disclosed herein has been given the variety denomination 'YUGOSTA03'.

BACKGROUND OF THE INVENTION

Parentage: 'YUGOSTA03' is a spontaneous, partial-plant branch mutation of a *Yucca guatemalensis* 'YUGOSTA02' plant (U.S. Plant Pat. No. 24,502), discovered in January of 2018. The mutation was discovered growing amongst a cultivated population of 'YUGOSTA02' plants at a commercial greenhouse in Honselerdijk, The Netherlands. The mutation was initially noted for its unique foliage variegation and compact growth habit. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'YUGOSTA03' is accomplished by way of rooting stem cuttings. Propagation was first performed in July of 2018 at the inventor's commercial greenhouse in Honselerdijk, the Netherlands. Through five subsequent generations, the unique features of this cultivar have proven to be stable and true to type.

SUMMARY OF THE INVENTION

The cultivar 'YUGOSTA03' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'YUGOSTA03'. These characteristics in combination distinguish 'YUGOSTA03' as a new and distinct *Yucca guatemalensis* cultivar:

1. *Yucca* 'YUGOSTA03' exhibits a compact growth habit with ensiform foliage that is borne on a short, unbranched stem; and
2. *Yucca* 'YUGOSTA03' exhibits juvenile adaxial foliar surfaces with longitudinal stripes that vary in color from darker green at the center of the lamina, to a combination of yellow and yellow-green adjacent to the central stripes, to lighter green towards the marginal zone, and a mixture of green and yellow-green at the margins; and
3. *Yucca* 'YUGOSTA03' exhibits mature adaxial foliar surfaces that are colored white with a green longitudinal stripe present at the midrib and a combination of green, dark green and greyed-green longitudinal stripes along the central zone of the lamina, adjacent to the midrib; and
4. *Yucca* 'YUGOSTA03' exhibits mature abaxial foliar surfaces that are colored with a mixture of white and green-white and longitudinally striped with a combination of green and greyed-green; and
5. *Yucca* 'YUGOSTA03' exhibits mature foliage that is margined with a mixture of green and yellow-green.

BOTANICAL DESCRIPTION OF THE PLANT

Figure 1:
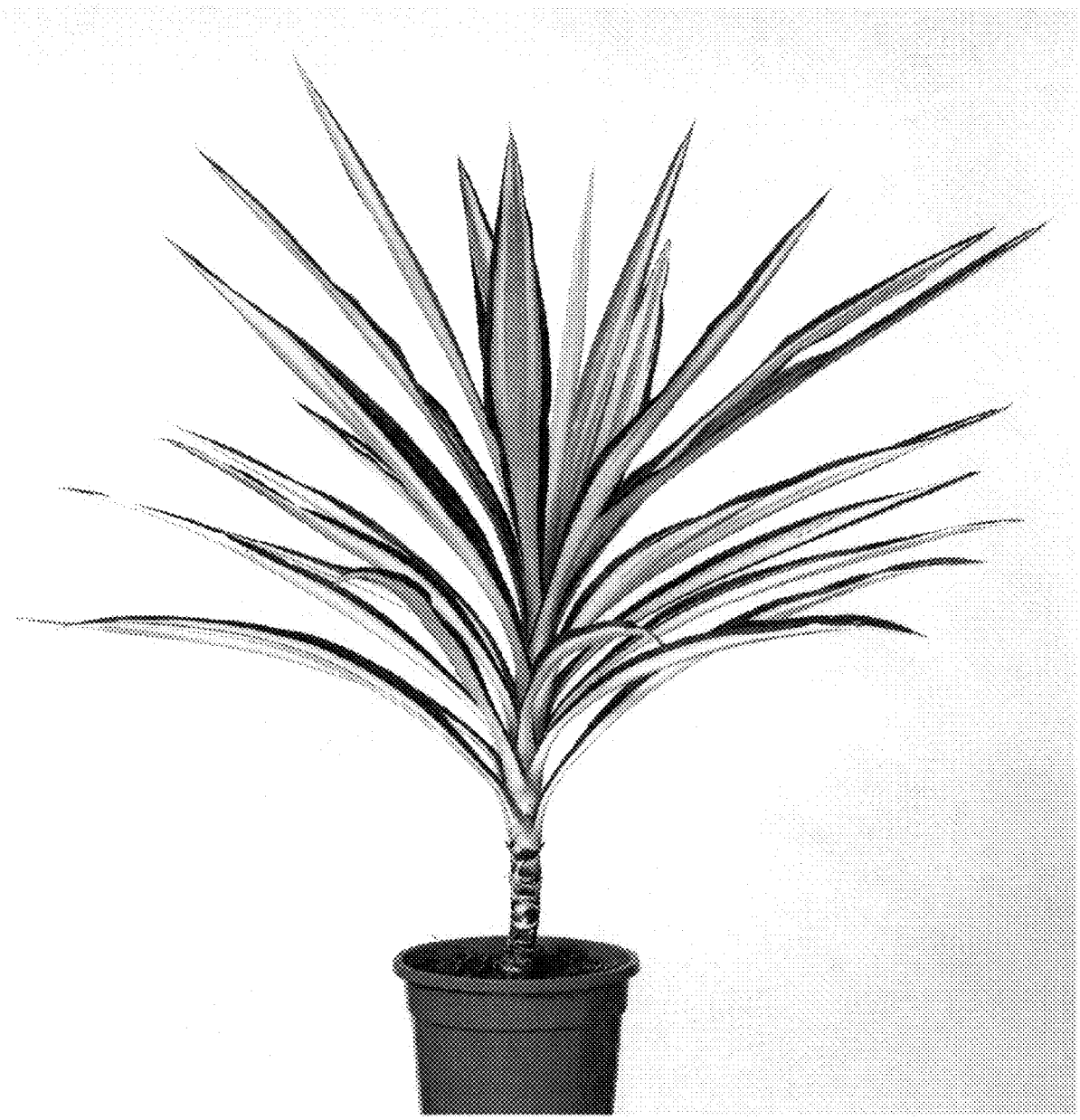
FIG. 1 illustrates, as nearly true as it is reasonably possible to make the same in color photographs of this type, an exemplary plant of 'YUGOSTA03' grown in Honselerdijk, The Netherlands. This plant, grown in a 17 cm nursery container, is approximately 8 months old from a rooted young plant.
Figure 2:
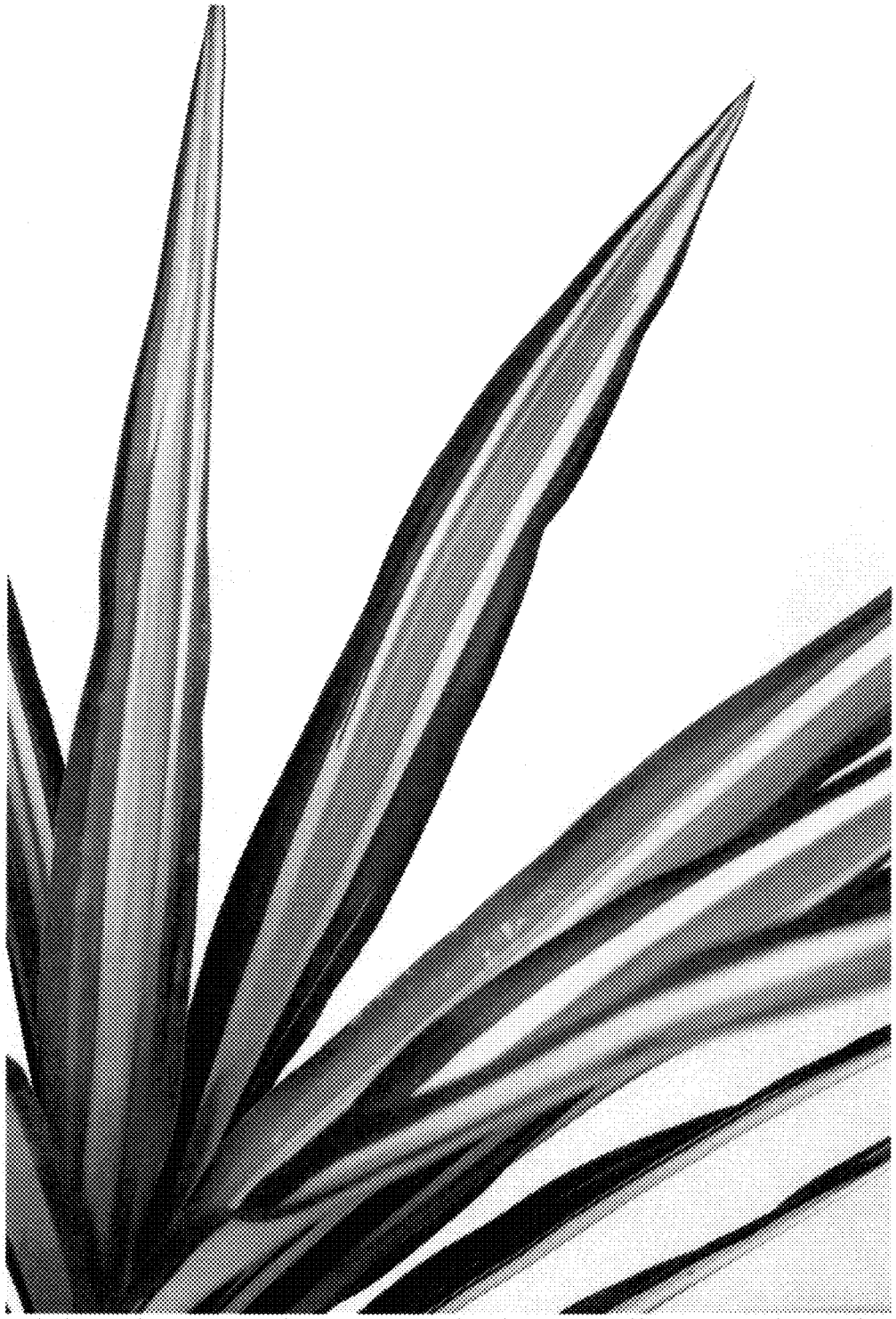
FIG. 2 illustrates, as nearly true as it is reasonably possible to make the same in color photographs of this type, the typical foliage of 'YUGOSTA03'.

The following observations and measurements, made in July of 2023, describe averages from a sample set of six specimens of 8-month-old 'YUGOSTA03' plants grown in 17 cm nursery pots in Honselerdijk, The Netherlands. Plants were produced using conventional greenhouse production protocols for *Yucca* sp. which consisted of growing under shade cloth, irrigating and fertilizing once a week during summer and once every two to three weeks in cool weather, maintaining an average ambient temperature of 20 degrees Celsius, and chemical control of thrips insects. No photoperiodic treatments or artificial light was given to the plants.

Those skilled in the art will appreciate that certain characteristics will vary with older or, conversely, with younger plants. 'YUGOSTA03' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'YUGOSTA03' and comparisons with the parent plant and most similar commercial *Yucca* cultivar known to the inventor are provided below.

Plant description:

*Growth habit*.—Compact, upright evergreen perennial with foliage born on a solitary short, unbranched stem.

*Plant profile*.—Broad obovate.

*Average height from base to top of foliage*.—64.5 cm.

*Average width*.—Average of 67.5 cm.

*Plant vigor*.—Moderately vigorous.

*Propagation details*.—Asexual propagation is accomplished by stem cuttings.

*Time to initiate roots*.—Approximately 5 weeks are required to initiate roots at 20 degrees Celsius.

*Time to produce a marketable* 17 *cm potted plant*.—Approximately 6 months.

*Disease and pest resistance or susceptibility*.—Neither tolerance nor resistance to normal diseases and pests of *Yucca guatemalensis* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching, characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—25.0 cm.

*Diameter*.—Average 1.9 cm.

*Internode length*.—Average 0.8 cm.

*Stem texture*.—Glabrous; smooth.

*Stem luster*.—Slightly glossy.

*Color, developing stems*.—Yellow-green, nearest to RHS 150D.

*Color, mature stems*.—Greyed-orange to brown, nearest to a combination of RHS 166A, 200B, and 200D.

*Color at the internodes*.—Yellow-green, nearest to RHS 146D.

*Color of the oldest wood*.—Brown, nearest to RHS 200D.

Foliage:

*Arrangement*.—Alternate to spiraled; distichous.

*Attachment*.—Sheathed.

*Division*.—Simple.

*Attitude*.—Near upright.

*Number of leaves per plant*.—28.

*Lamina*.—Dimensions — 45.3 cm long and 4.4 cm wide, on average. Shape — Ensiform. Aspect — Slightly spiraled, with the distalmost portion on the lamina pointing downward. Apex — Narrowly acute with a short, pungent tip. Base — Sheathed. Sheath — Length — 2.7 cm. Width — 1.9 cm. Color, adaxial surface — Green-white, nearest to RHS 157C. Color, abaxial surface — Green-white, nearest to RHS 157C. Margin — Entire; finely dentate with approximately 25 teeth per one centimeter, on average; teeth 0.3 mm tall and colored yellow-green, nearest to RHS 147C; margins are coarsely undulated. Texture and luster of adaxial surface — Smooth, glabrous, and slightly glossy. Texture and luster of abaxial surface — Smooth to slightly rough to the touch, glabrous, and matte. Color — Juvenile foliage, adaxial surface — Patterned with distinct longitudinal stripes that vary in color from darker green at the center of the lamina, to a combination of yellow and yellow-green adjacent to the central stripes, to lighter green towards the marginal zone, and a mixture of green and yellow-green at the margins. Central stripes are green, nearest to a mixture of RHS 138B and 138C; stripes adjacent to the central stripes are a combination of yellow and yellow-green, nearest to RHS 4C and 154D; stripes adjacent to the marginal stripes are lighter green, nearest to in between RHS 143A and 143B; margins are colored with a mixture of green and yellow-green, nearest to RHS NN137A and 147A. Juvenile foliage, abaxial surface — Patterned with distinct longitudinal stripes that vary in color from a combination of green and greyed-green at the center of the lamina, to yellow adjacent to the central stripes, to a combination of green and greyed-green towards the marginal zone, and dark green at the margins. Central stripes are a combination of green and greyed-green, nearest to RHS 138B and 191B; stripes adjacent to the central stripes are yellow, nearest to RHS 5D; stripes adjacent to the marginal stripes are a combination of green and greyed-green, nearest to RHS 138C and 191B; margins are colored green, nearest to RHS NN137A. Mature foliage, adaxial surface — White, nearest to RHS 155D; narrow, green longitudinal stripe at the midrib, nearest to in between RHS 143A and 143B; narrow, green, dark green and greyed-green longitudinal stripes along the central zone of the lamina, adjacent to the midrib, nearest to RHS NN137A, NN137B, NN137C, 143A, 143B, and 191B; margined with a mixture of green and yellow-green, nearest to RHS NN137A and 147A. Mature foliage, abaxial surface — Nearest to a mixture of white and green-white, RHS 155D, 157C, and 157C; longitudinally striped with a combination of green and greyed-green, nearest to RHS NN137A, 191C, and 191D; margined with a mixture of green and yellow-green, nearest to RHS NN137A and 147A. Venation — Pattern — Parallel. Color, adaxial surface — All veins are indistinguishable from the surrounding foliage. Color, abaxial surface — The main vein is green-white, nearest to RHS 157C. All other veins are indistinguishable from the surrounding foliage.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'YUGOSTA03' may be distinguished from its parent, *Yucca guatemalensis* 'YUGOSTA02' (U.S. Plant Pat. No. 24,502), by the characteristics described in Table 1.

TABLE 1

| Characteristic | 'YUGOSTA03' | 'YUGOSTA02' |
|---|---|---|
| Juvenile foliage coloration; adaxial surface. | Distinct longitudinal stripes that vary in color from darker green at the center of the lamina, to a combination of yellow and yellow-green adjacent to the central stripes, to lighter green towards the marginal zone, and a mixture of green and yellow-green at the margins. | Striped with a combination of yellow-green and light green along the central portion of the lamina with darker green margins. |
| Mature foliage coloration; adaxial surface. | White; narrow, green longitudinal stripe present at the midrib; a combination of narrow green, dark green and greyed-green longitudinal stripes along the central zone of the lamina, adjacent to the midrib; margined with a mixture of green and yellow-green. | Striped with a combination of yellow-white and greyed-green along the central portion of the lamina, though predominantly colored greyed-green, with broad dark green margins. |
| Mature foliage coloration; abaxial surface. | A mixture of white and green-white and longitudinally striped with a combination of green and greyed-green; margined with a mixture of green and yellow-green. | Striped with a combination of yellow-white and greyed-green along the central portion of the lamina, though generally appearing as a mixture of light yellow-green and green-yellow, with broad dark green margins. |

Plants of the new cultivar 'YUGOSTA03' are similar to the closest known commercial comparator, *Yucca* 'Silver Star' (not patented). The two plants may be distinguished from one another by the characteristics described in Table 2.

TABLE 2

| Characteristic | 'YUGOSTA03' | 'Silver Star' |
|---|---|---|
| Juvenile foliage coloration; adaxial surface. | Distinct longitudinal stripes that vary in color from darker green at the center of the lamina, to a combination of yellow and yellow-green adjacent to the central stripes, to lighter green towards the marginal zone, and a mixture of green and yellow-green at the margins. | Striped with a combination of yellow-green and light greyed-green along the central portion of the lamina with darker green margins. |
| Mature foliage coloration; adaxial surface. | White; narrow, green longitudinal stripe present at the midrib; a combination of narrow green, dark green and greyed-green longitudinal stripes along the central zone of the lamina, adjacent to the midrib; margined with a mixture of green and yellow-green. | Light greyed-green with broad, dark green margins; occasionally streaked with green-yellow along the margin zones. |
| Mature foliage coloration; abaxial surface. | A mixture of white and green-white and longitudinally striped with a combination of green and greyed-green; margined with a mixture of green and yellow-green. | Very light greyed-green and margined dark green. |

That which is claimed is:

1. A new and distinct cultivar of *Yucca* plant named 'YUGOSTA03', substantially as described and illustrated herein.

* * * * *